United States Patent [19]
Lococo

[11] 4,378,211
[45] Mar. 29, 1983

[54] DENTAL IMPRESSION TRAY

[76] Inventor: Michael P. Lococo, 4927 Victoria Ave., Niagara Falls, Ontario, Canada, L2E 1X1

[21] Appl. No.: 323,978

[22] Filed: Nov. 23, 1981

[30] Foreign Application Priority Data

Jul. 7, 1981 [CA] Canada .................... 381626

[51] Int. Cl.³ .............................................. A61C 9/00
[52] U.S. Cl. ........................................ 433/36; 433/37; 433/89
[58] Field of Search ............... 433/36, 37, 80, 82, 433/83, 89, 90

[56] References Cited

U.S. PATENT DOCUMENTS

| | | | |
|---|---|---|---|
| 2,155,334 | 4/1939 | Sitkin et al. | 433/36 |
| 2,349,607 | 5/1944 | Berger | 433/36 |
| 2,428,773 | 10/1947 | Beresin et al. | 433/36 |
| 2,452,903 | 11/1948 | Coffey | 433/36 |
| 2,458,145 | 1/1949 | Coffey | 433/36 |
| 3,226,828 | 1/1966 | Spalten | 433/37 |
| 3,304,608 | 2/1967 | Frohnecke | 433/40 |
| 3,357,104 | 12/1967 | Greene et al. | 433/38 |
| 3,390,457 | 7/1968 | Zatz | 433/36 |
| 3,722,097 | 3/1973 | Colman et al. | 433/36 |

FOREIGN PATENT DOCUMENTS 417485 12/1943 Canada .
1007078 3/1977 Canada .

Primary Examiner—Gene Mancene
Assistant Examiner—John J. Wilson
Attorney, Agent, or Firm—Stevens, Davis, Miller & Mosher

[57] ABSTRACT

A combined dental impression tray with a syringe is provided, wherein the communication between the syringe and the tray is effected, in the most preferred embodiment, by way of a side opening in the wall of the barrel of the syringe. The opening communicates with the bottom section of the tray and is very short compared to the diameter or cross-sectional area of the passage for the impression material. The opening is arranged such that it can be closed by the piston of the syringe while a first impression of the tissue area is taken. A device detachably secured to the tray apparatus is also provided to facilitate cutting out of a portion of the dental mixture, the cutting device being preferably of the type of a reciprocating tubular cutting die whose edge engages the bottom wall of the tray at a close spacing about the said opening. The advance in the art is in an arrangement which avoids any narrow passages between the syringe and the tray or channels difficult to clean and causing entrapment of air bubbles which may result in a reduced quality of the impression.

9 Claims, 5 Drawing Figures

DENTAL IMPRESSION TRAY

The present invention relates to dental impression trays and in particular to dental impression trays of the type utilizing a syringe mechanism for increasing the pressure at which the impression material is forced into the tray.

The process of taking a dental impression includes the steps of preparing an impression mixture, usually a fairly fast hardening mixture, which is then placed into a tray and, if the tray is provided with a syringe, to the syringe. The tray is then pressed to the desired area, usually having a soft rubber or the like seal around its edge, to provide at least a partial seal against the tissue about the rim of the tray. The impression material is then forced into the cavity of the tray, allowed to harden and then removed.

A great number of combined impression trays and syringes have long been known from prior art. Reference may be had, for instance, to Canadian Pat. No. 417,485, issued Dec. 28, 1943, to Conway et al., to Canadian Pat. No. 1,007,078, issued Mar. 22, 1977 to Lopex et al., U.S. Pat. No. 2,155,334 issued Apr. 18, 1939 to Sitkin et al., U.S. Pat. No. 2,349,607, issued May 23, 1944 to H. R. Berger, U.S. Pat. No. 2,428,773 issued Oct. 14, 1947 to Beresin et al., U.S. Pat. No. 2,452,903, issued Nov. 2, 1948 to Coffey, U.S. Pat. No. 2,458,145 issued Jan. 4, 1949 to E. G. Coffey, and U.S. Pat. No. 3,722,097, issued Mar. 27, 1973 to Colman et al, all of the foregoing prior art references being typical of different attempts made by artisans in order to improve the dental impression tray of the type mentioned at the outset.

Despite apparently intensive efforts by different artisans, a dental impression tray utilizing a syringe is not widely used in dentistry and generally has not found acceptance in the art. To the best knowledge of the applicant herewith, most dentists nowadays utilize an impression tray without a syringe. The procedure accepted nowadays is that a first, relatively thick or heavy bodied impression mixture is placed into a tray, whereupon the tray is pressed against the tissues surrounding the area whose impression is to be eventually obtained. Upon hardening of the relatively thick impression material, a reasonably accurate impression of the soft tissue is obtained. Then, the impression material is cut out of the bottom section of the impression tray leaving only a relatively narrow margin around the edge of the tray. The tray is then filled in with a relatively thin or light bodied impression material and pressed again to the same area. The first impression aids in preventing free escape of the thin impression material from within the tray as the tray is subjected to pressure thus assisting in providing the impression of the tooth.

The accuracy of an impression provided by the aforesaid method is limited due to a relatively small pressure at which the tray can be pressed against the area of soft tissue surrounding the tooth or the like to be impressed. Yet, attempts to combine the tray with a syringe have failed mainly due to the fact that problems have been experienced with air entrapment in the syringe, in cleaning the syringe, and in relatively bulky overall structure.

It is an object of the present invention to provide an improved combination of the syringe and impression tray capable of repeated use and relatively easy to operate, particularly with respect to the above method utilizing two different thickness impression materials.

In general terms, the present invention provides a dental impression tray, comprising, in combination: a tray section including a bottom wall surface, side wall surfaces and end wall surfaces defining a cavity for receiving a hardening dental impression mixture; a syringe including a barrel section, piston means and piston actuating means for displacing said piston means within said barrel; communication passage between said barrel section and said cavity for transfer of the mixture from said barrel into said cavity; said communication passage including an inlet end section at said barrel, and an outlet end section generally coincident with said bottom wall; the average cross-sectional area of the passage being a multiple of the square of the length thereof.

Preferably, the length of said passage as measured between the end sections thereof is generally equal to or less than the combined thickness of said bottom wall and a side wall of said barrel. In accordance with another feature of the present invention, the cross-sectional area of said passage is of a generally uniform size throughout the length of said passage. In accordance with a particularly preferred embodiment of the present invention, the inlet end section is provided in a side wall of said barrel. The piston is preferably of the length sufficient to cover the entire inlet end section of said passage thus being capable of shutting off the communication between the barrel and the tray. The barrel of the syringe is preferably made integral with at least a part of the bottom wall of the tray to reduce the overall thickness of the side wall of the barrel and of the bottom wall of the tray to thus reduce the length of said passage to a minimum. Accordingly, when the piston assumes its "closed" state overlapping the inlet of the passage, the side of the piston coincident with the opening is generally flush with the bottom of the tray and is thus relatively easy to clean and to remove the part of the hardened relatively thick impression material utilized in the first of the two steps of taking the impression, as referred to above.

In accordance with another feature of the present invention, a dental impression tray apparatus is provided generally as referred to above but further comprising a cutting device adapted to be removably secured to the apparatus and comprising: a cutting die of a tubular cross-section and having a cutting edge at one end thereof, said cutting edge being generally complementary with the shape and size of cross-sectional configuration of a discharge end of said communication passage; centering means for centering said cutting edge in a coaxial relationship relative to the communication passage; and die actuation means for moving said cutting die within said cavity in a direction towards or away from said bottom wall surface, whereby said cutting edge is capable of producing a cutout passage in dental impression mixture contained in said cavity, the cutout passage forming generally an extension of said communication passage.

The invention will now be described with reference to the accompanying simplified drawings wherein.

Figure 1:
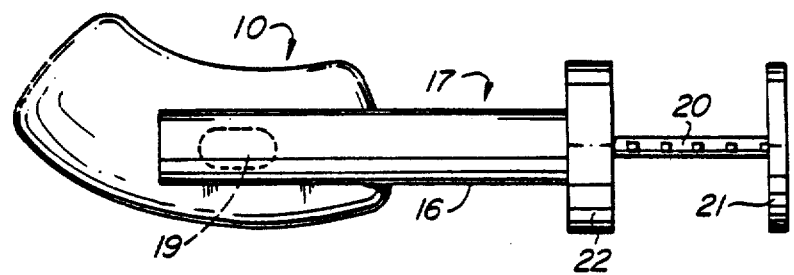
FIG. 1 is a simplified top view of a dental impression tray of the present invention.
Figure 2:
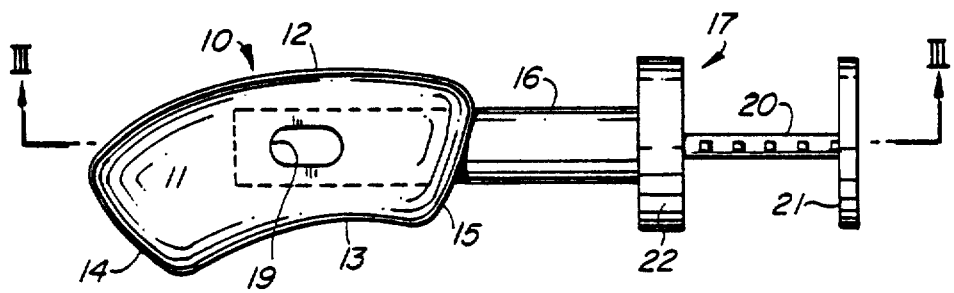
FIG. 2 is a bottom view thereof.

Reference numeral 10 designates a tray section comprised of a bottom wall 11, two side walls 12, 13 and two end walls 14, 15. The bottom wall 11 is integral with a part of a side wall of a cylinder or barrel 16 of a syringe 17. A piston 18 is received slidably within the barrel 16. The barrel 16 communicates with the interior or cavity of the tray section 10 through an opening 19 whose length, in this embodiment, is equal to the thickness of the bottom wall 11, as best seen from FIG. 3. Accordingly, the length of the opening 19 is very short compared to its diameter determining the cross-sectional area of the passage or opening 19. The piston 18 is connected to a piston rod 20 having a handle 21 at its axial end remote from the piston 18. A removable end section 22 is secured to the axial end of the barrel 16 remote from the opening 19. The piston rod 20 is provided with a plurality of protrusions and depressions serving the purpose of enabling the locking of the piston rod relative to the end section 22, as is well known in the art of syringes. For instance, the piston rod 20 may be of an oval cross-section complementary with the cross-section of a central passage in the end section 22 for the piston rod, with the depressions provided at respective ends of the oval cross-section to enable the turning of the piston-rod and of the piston by 90° thus engaging the end section plate 22 with the piston rod to prevent axial displacement of the piston rod from a predetermined position.

Figure 3:
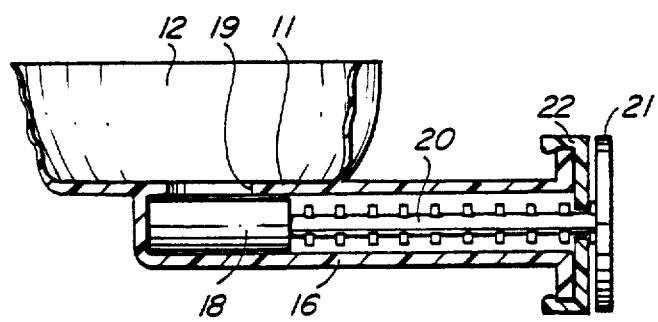
FIG. 3 is a section III—III of FIG. 2, showing the piston of the syringe in a position wherein it covers the passage communicating the barrel of the syringe with the tray.

In operation, the piston 18 is first moved fully to the left hand side of the barrel 16 as viewed in the figures, thus covering the opening 19 (FIG. 3). The tray is now ready for the first step of taking the impression, namely for filling with a relatively thick impression material. Then, the tray is pressed against the area whose impression is to be taken, to obtain impression of the soft tissue near the peripheral edge portion 23 of the tray section 10. On hardening of the material, the part thereof interiorly of the area surrounding the edge portion is removed. The tray is now ready for receiving the second, thinner impression material. The piston rod 20 and the end section 22 is released from the barrel 16 and the piston 18 is removed from the barrel. The light bodied material is placed into the barrel 16 and the piston 18 reinserted into the barrel 16. The end section is secured to the barrel 16. The piston 18 is then actuated until a full, continuous volume of the impression material flows through the opening 19 into the tray, indicating that there is virtually no air within the portion of the barrel 16 holding the material. The piston rod 20 is now locked relative to the end section 22 and the remaining space of the tray interior filled with the light bodied impression material up to the impression rim produced at the outset from the heavy bodied material. Then, the tray is applied and pressed to the particular region until the impression rim contacts the tissue. A further movement of the piston (after unlocking the piston rod from the end section 22) increases the pressure within the tray resulting in an improved accuracy of the obtained impression. The cleaning of the tray does not pose a serious problem with respect to the material remaining within the barrel 16, since the barrel 16 is accessible both through the opening 19 and through the opposite axial end of the barrel 16, upon removal of the end section 22 and of the piston 18.

Figure 4:
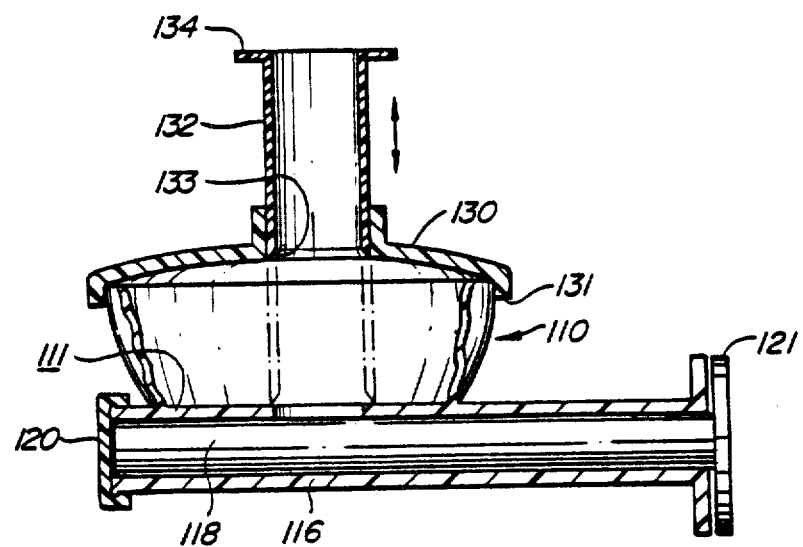
FIG. 4 is a sectional view similar to that of FIG. 3 but showing a slightly modified and simplified version of the impression tray of the present invention, shown in a state wherein a further feature of the present invention, namely a cutting device is secured to the impression tray apparatus.

Turning now to the embodiment shown in FIG. 4, a modified version of the impression tray is shown.

Like the preceding embodiment, there is a tray section 110 comprised of a bottom wall 111 having two side walls and two end walls. The bottom wall 111 is integral with a part of a side wall of a cylinder 116 receiving a piston 118 slidable within the barrel 116. The barrel 116 communicates with the interior or cavity of the tray section 110 through an opening 119 whose length, again, is equal to the thickness of the bottom wall 111. The barrel 116 is provided at its end faced by the free end portion of the piston 118 with a closure cap 120, while the opposite end of the piston 118 is provided with a handle 121. Thus, the entire piston assembly is formed by a smooth cylindric piston 118 extending up to the handle 121.

The advantage of the embodiment shown in FIG. 4 is in that it has a smoother surface of the piston part. The piston 118 is easy to be removed from the barrel 116. On removal of the cap 120, the barrel 116 is relatively easy to be cleaned, particularly if one considers the actual size of the opening 119.

Figure 5:
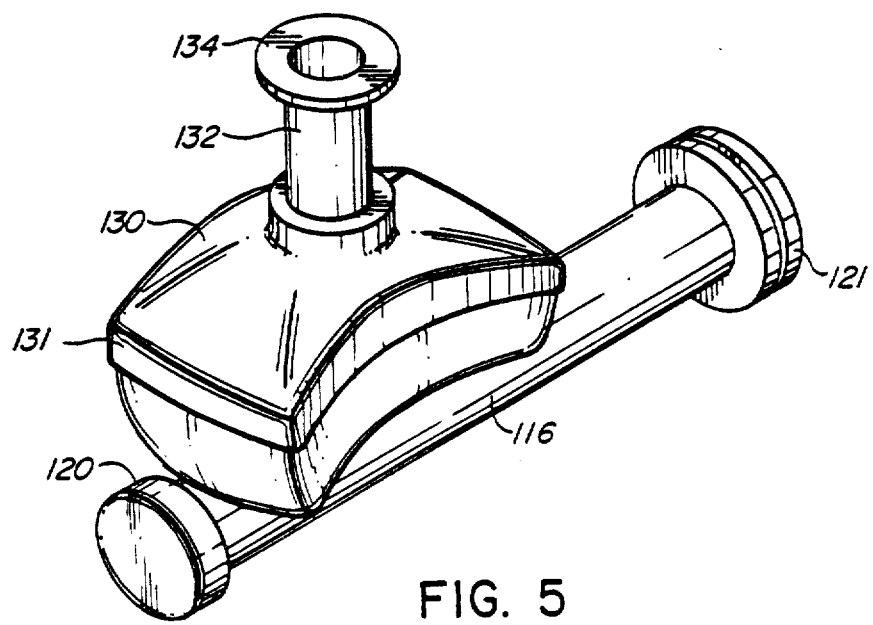
FIG. 5 is a perspective view of one embodiment of the cutting device shown in FIG. 4.

The embodiment of FIG. 4 is shown with a preferred embodiment of a device for cutting out a part of the impression material following the making of the first impression. Instead of the usual use of a scalpel to cut out the material before introducing the thin impression material, a device as shown in FIGS. 4 and 5 can be used. It consists of an upwardly arched top wall 130 having a downwardly turned lip 131 which is complementary with the peripheral shape of the upper rim of the tray section 110, as best seen in FIG. 4. An upwardly directed cylindric section 132 slidably receives a tubular cutting die 133 whose top end is provided with a flange 134. The bottom end of the cutting die 133 has a cutting edge 134, which is adapted to engage a generally flat section of the bottom wall 111 at a very close spacing about the periphery of the opening 119, as shown by broken lines in FIG. 4. Thus, assuming that an impression has been taken using the relatively thick dental impression material, the cutting device can be attached to the tray, the cutting die 133 pressed down against the bottom wall 111 and the material is then relatively easy to be removed from the tray. The whole operation is simple and very accurate and provides relatively limited space for the subsequent introduction of the relatively thin impression material for the taking of the second impression.

It will be immediately appreciated by those skilled in the art that the centering of the cutting die and the shape of the cutting die per se is subject to a vast number of different modifications. The securement of the die to the apparatus can be effected to different parts of the device without departing from the present invention.

The described embodiment is believed to the the best mode of utilizing the present invention since it offers an extreme simplicity in structure and thus a relatively low manufacturing cost. Due to the piston 18 being capable of covering the opening 19 when the first, preliminary impression of the tissue is taken, it is relatively easy to remove the excessive impression part of the first, relatively thick material to make the tray ready for the relatively thin material.

Those skilled in the art will nevertheless appreciate that many further modifications of the impression tray of the present invention may exist departing, to a greater or to a lesser degree, from the embodiments shown, without departing from the scope of the present invention as set forth in the accompanying claims.

The embodiments of the invention in which an exclusive property or privilege is claimed are defined as follows:

1. Dental impression tray comprising, in combination:
   (a) a tray section including a bottom wall surface, side wall surfaces and end wall surfaces defining a cavity for receiving a hardening dental impression mixture;
   (b) a syringe including a barrel section, piston means and piston actuating means for displacing said piston means within said barrel;
   (c) communication passage between said barrel section and said cavity for transfer of the mixture from said barrel into said cavity;
   (d) said communication passage including an inlet end section at said barrel, and an outlet end section generally coincident with said bottom wall;
   (e) the average cross-sectional area of the passage being a multiple of the square of the length thereof;
   (f) the length of the passage as measured between the end sections thereof being equal to or less than the combined thickness of said bottom wall and a side wall of said barrel.

2. Dental impression tray as claimed in claim 1, wherein the cross-sectional area of said passage is of a generally uniform size throughout the length of said passage.

3. Dental impression tray as claimed in claim 1, wherein said inlet end section is provided in a side wall of said barrel.

4. Dental impression tray as claimed in claim 1, wherein said inlet end section is provided in a side wall of said barrel and wherein axial length of said piston means is such that the piston means is capable of covering the inlet end section to shut-off the communication between said barrel and said tray when the piston means assumes a predetermined axial position relative to the barrel.

5. Dental impression tray as claimed in claim 1, wherein said inlet end section is provided in a side wall of said barrel and wherein axial length of said piston means is such that the piston means is capable of generally fully covering the inlet end section to shut-off the communication between said barrel and said tray when the piston means assumes a predetermined axial position relative to the barrel, a side wall section of said barrel section at the inlet end section being generally integral with a section of the bottom wall of the tray at said outlet end section, whereby a side portion of said piston means is generally flush with said bottom wall surface when said piston means covers said inlet end section.

6. Dental impression tray as claimed in claim 1, wherein said inlet end section is provided in a side wall of said barrel and wherein axial length of said piston means is such that the piston means is capable of generally fully covering the inlet end section to shut-off the communcation between said barrel and said tray when the piston means assumes a predetermined axial position relative to the barrel, a side wall section of said barrel section at the inlet end section being generally integral with a section of the bottom wall of the tray at said outlet end section, whereby a side portion of said piston means is generally flush with said bottom wall surface when said piston means covers said inlet end section, said predetermined axial position of the piston means being generally coincident with the position thereof at the end of a stroke forcing the contents of the barrel through said passage into said cavity.

7. Dental impression tray apparatus as claimed in claim 1, further including a cutting device adapted to be removably secured to the apparatus and comprising:
   (a) a cutting die of a tubular cross-section and having a cutting edge at one end thereof, said cutting edge being generally complementary with the shape and size of cross-sectional configuration of a discharge end of said communication passage;
   (b) centering means for centering said cutting edge in a coaxial relationship relative to the communication passage; and
   (c) die actuation means for moving said cutting die within said cavity in a direction towards or away from said bottom wall surface,
   whereby said cutting edge is capable of producing a cutout passage in dental impression mixture contained in said cavity, the cutout passage forming generally an extension of said communication passage.

8. Dental impression tray apparatus as claimed in claim 1, further including a cutting device adapted to be removably secured to the apparatus and comprising:
   (a) cutting die of a tubular cross-section and having a cutting edge at one end thereof, said cutting edge being generally complementary with the shape of and being slightly greater than the cross-sectional configuration of a discharge end of said communication passage;
   (b) centering means for centering said cutting edge in a coaxial relationship relative to the communication passage;
   (c) die actuation means for moving said cutting die within said cavity in a direction towards or away from said bottom wall surface,
   whereby said cutting edge is capable of producing a cutout passage in dental impression mixture contained in said cavity, the cutout passage forming generally an extension of said communication passage.

9. Dental impression tray apparatus as claimed in claim 1, further including a cutting device adapted to be removably secured to the apparatus and comprising:
   (a) cutting die of a tubular cross-section and having a cutting edge at one end thereof, said cutting edge being generally complementary with the shape of and being slightly greater in size than the cross-sectional configuration of a discharge end of said communication passage;
   (b) centering means for centering said cutting edge in a coaxial relationship relative to the communication passage;
   (c) die actuation means for moving said cutting die within said cavity in a direction towards or away from said bottom wall surface;
   (d) said bottom wall surface including a generally flat wall section surrounding said discharge end, said cutting edge being disposed within a plane generally perpendicular to the direction of said reciprocating of the die;
   (e) said centering means being so arranged and disposed that on attachment of the cutting device to the apparatus, the cutting edge abuts, at its one extreme position, against the bottom wall section at a continuous locus, closely spaced from and adjacent to said discharge end.

* * * * *